US00PP16951P3

(12) United States Plant Patent
Meilland

(10) Patent No.: US PP16,951 P3
(45) Date of Patent: Aug. 8, 2006

(54) HYBRID TEA ROSE PLANT NAMED 'MEIFAISSEL'

(50) Latin Name: *Rosa hybrida*
Varietal Denomination: Meifaissel

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 74 days.

(21) Appl. No.: 11/034,250

(22) Filed: Jan. 13, 2005

(65) Prior Publication Data

US 2006/0156446 P1 Jul. 13, 2006

(51) Int. Cl.
*A01H 5/00* (2006.01)

(52) U.S. Cl. ..... Plt./133

(58) Field of Classification Search ..... Plt./130, Plt./133, 134, 141, 144, 145
See application file for complete search history.

(56) References Cited

U.S. PATENT DOCUMENTS

PP9,274 P * 9/1995 Olesen et al. ..... Plt./133

* cited by examiner

*Primary Examiner*—Howard J. Locker
(74) *Attorney, Agent, or Firm*—Buchanan Ingersoll PC

(57) ABSTRACT

A new and distinct variety of Hybrid Tea rose plant is provided which abundantly forms on a nearly continuous basis attractive white high-pointed blossoms having a very strong fragrance. The plant exhibits a semi-erect growth habit, and dense dark green foliage with a semi-glossy aspect. Good tolerance to Oidium and Black Spot is displayed. The attractive dark green foliage contrasts nicely with the pure white blossom coloration. The new variety is particularly well suited for growing as attractive ornamentation in the landscape.

1 Drawing Sheet

Figures 1, 2, 3, 4, 5, 6, 7, 8, 9, 10, 11, 12, 13, 14, 15, 16:
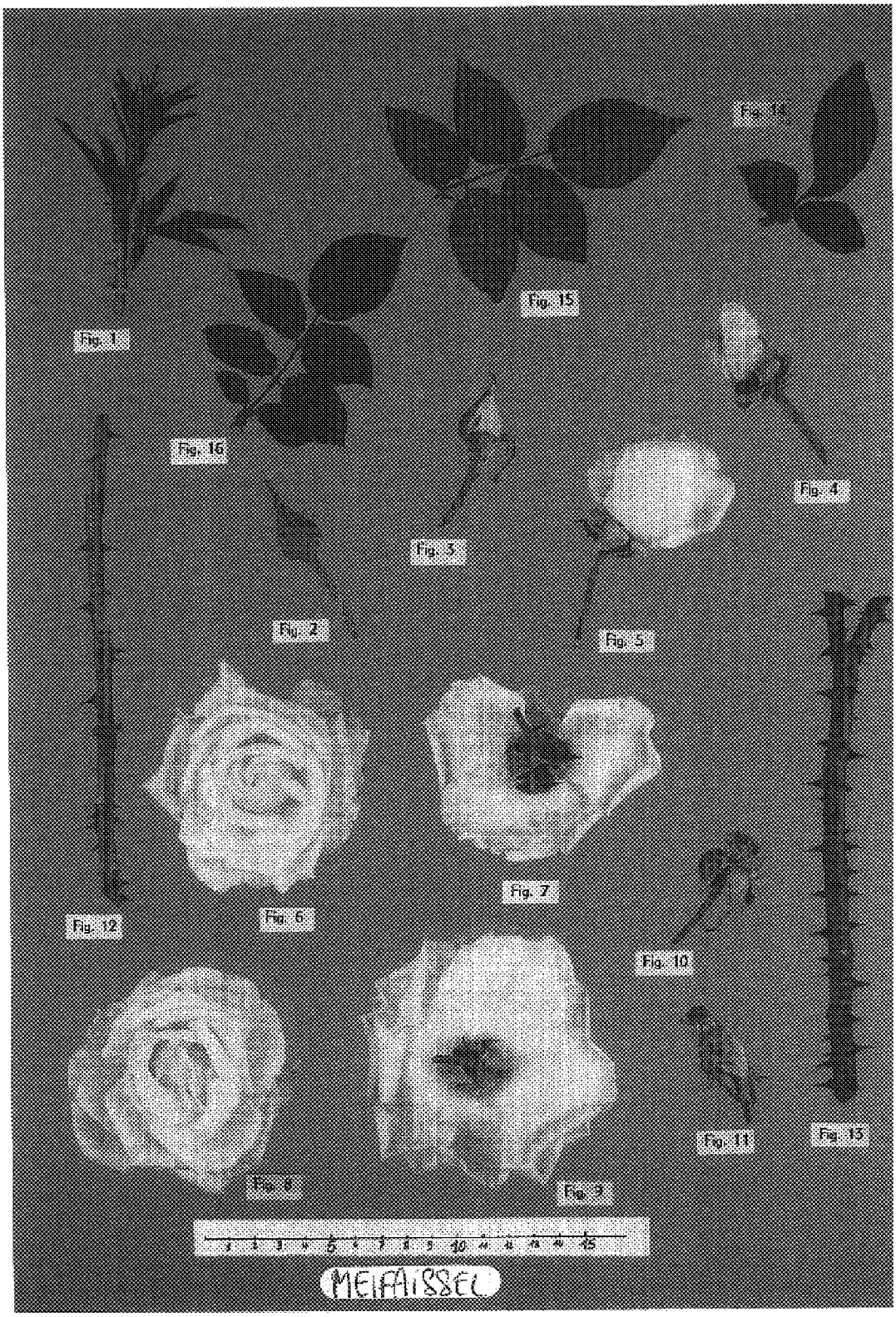

Botanical/commercial classification: *Rosa hybrida*/Hybrid Tea Rose.
Varietal denomination: cv. 'Meifaissel'.

SUMMARY OF THE INVENTION

The new variety of *Rosa hybrida* Hybrid Tea rose plant was created by artificial pollination wherein two parents were crossed which previously had been studied in the hope that they would contribute the desired characteristics. The female parent (i.e., the seed parent) was the 'Meban' variety (non-patented in the United States). The 'Meban' variety sometimes is known as the 'White Knight' variety. The male parent (i.e., the pollen parent) was the product of the cross of the 'Poulari' variety (U.S. Plant Pat. No. 9,274) and the 'Lady Sylvia' variety (non-patented in the United States). The 'Poulari' variety sometimes is known as the 'Karen Blixen' variety. The parentage of the new variety can be summarized as follows:

'Meban'×('Poulari'×'Lady Sylvia').

The seeds resulting from the above pollination were sown and small plants were obtained which were physically and biologically different from each other. Selective study resulted in the identification of a single plant of the new variety.

It was found that the new variety of the present invention (a) exhibits a very vigorous semi-erect growth habit, (b) abundantly forms on a nearly continuous basis attractive white high-centered blossoms having a very strong fragrance, (c) forms dense dark green foliage having a semi-glossy aspect that contrasts well with the blossom coloration, and (d) is particularly well suited for growing as attractive ornamentation in the landscape.

The tolerance to Oidium and Black Spot is good, and the white blossom coloration is stable. The very strong blossom fragrance is a combination of sweet rose and banana.

The new variety well meets the needs of the horticultural industry and can be grown to advantage in parks and gardens where attractive ornamentation is desired.

The new variety can be readily distinguished from its ancestors. For instance, the 'Meban' variety forms white blossoms having approximately 33 petals having no fragrance and light green foliage. The 'Poulari' variety forms blossoms in clusters having a very slight fragrance and medium green glossy foliage. The 'Lady Sylvia' variety forms light pink blossoms.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meifaissel', and is being marketed under the QUEEN MARY 2 trademark.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately 18 months of age and were observed during September while budded on *Rosa froebelli* understock and growing outdoors at Le Cannet des Maures, Var, France.

Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of eighteen month-old plants during September while budded on *Rosa froebelli* understock and growing outdoors at Le Cannet des Maures, Var, France.

Class: Hybrid Tea.

Plant:

*Height.*—Approximately 80 to 90 cm on average at the end of the growing season.

*Width.*—Approximately 60 to 70 cm on average at the end of the growing season.

*Habit.*—Semi-erect.

Branches:

*Color.*—Young stems: near Green Group 137C. Adult wood: near Green Group 137B.

*Thorns.*—Size and quantity: on 18 cm of young stems approximately 30 on average more than 5 mm in length and commonly none less than 5 mm in length, and on 19 mm of adult stems approximately 50 on average more than 5 mm in length and commonly none less than 5 mm in length. Color: near Greyed-Orange Group 175A on young stems, and near Greyed-Orange Group 166A on adult stems. Configuration: rather upright and curved downwards on the upper surface and concave under surface.

Leaves:

*Stipules.*—Adnate, pectinate, and rather broad.

*Petioles.*—Upper surface: near Green Group 131A in coloration. Under surface: near Yellow-Green Group 146B in coloration. Length: approximately 1.8 to 2 cm for the terminal leaflet.

*Leaflets.*—Number: 3, and most often 5 and 7. Shape: elliptical and lanceolate with a rounded base and an acuminate tip (as illustrated). Size: the terminal leaflets commonly are approximately 4 to 5 cm in length and approximately 3 cm in width on average. Serration: single and fine (as illustrated). Texture: firm. General appearance: dense, dark green with a semi-glossy aspect, and thick. Color (young foliage): Upper surface: near Green Group 137A suffused with some near Red Group 47A. Under surface: near Green Group 137C suffused with Red Group 47A. Color (adult foliage): Upper surface: near Green Group 131A. Under surface: near Yellow-Green Group 147A.

Inflorescence:

*Number of flowers.*—Commonly one flower per stem, and sometimes up to three flowers per stem.

*Peduncle.*—Rigid, near Green Group 137C in coloration, and the length is approximately 5 to 6 cm on average.

*Sepals.*—Upper surface: consistent and near Green Group 137D in coloration. Under surface: tomentose and near Green Group 138C in coloration. Configuration: elongated with small extensions (as illustrated).

*Buds.*—Shape: elongated. Size: medium (as illustrated). Length: approximately 2 cm on average. Color: Upper surface: near White Group 155A as the calyx breaks. Under surface: near White Group 155A and slightly suffused with Yellow-Green Group 145C as the calyx breaks. Basal petal spot: none.

*Flower.*—Shape: high-centered. Diameter: approximately 8 to 9 cm on average. Color (when blooming): Upper surface: near Yellow-White Group 158C. Under surface: near Yellow-White Group 158D. Basal petal spot: none. Discoloration: none observed. Fragrance: very strong and resembles sweet rose and banana. Lasting quality: the blossoms commonly last approximately 10 days on the plant on average. Petal number: approximately 25 or 26 on average under normal growing conditions. Petaloids: none observed. Petal shape: without undulation and with slight reflexing at the margin. Petal arrangement: imbricated. Petal drop: good with the petals commonly detaching cleanly before drying. Stamen number: approximately 250 on average. Petal texture: consistent. Anthers: regularly arranged around the styles, and near Orange Group 24C in coloration. Pollen: present and near Orange Group 24C in coloration. Filaments: near Yellow Group 4D in coloration, and approximately 0.4 cm in length on average. Pistils: approximately 195 on average. Stigmas: near Red Group 45B in coloration, and approximately 0.1 cm in size. Styles: near Red Group 45B in coloration, and approximately 0.5 to 0.6 cm in length on average. Receptacle: smooth, near Green Group 137D in coloration, and funnel-shaped in longitudinal section. The length commonly is approximately 0.8 to 1 cm on average and the width commonly is approximately 0.6 to 0.8 cm on average. Hips: none observed.

Development:

*Vegetation.*—Strong.

*Blooming.*—Very abundant and nearly continuous.

*Resistance to diseases.*—Good tolerance to Oidium and Black Spot.

*Aptitude to bear fruit.*—None observed during observations to date.

*Winter hardiness.*—Good.

I claim:

1. A new and distinct Hybrid Tea rose plant characterized by the following combination of characteristics:

(a) exhibits a very vigorous semi-erect growth habit;

(b) abundantly forms on a nearly continuous basis attractive white high-centered blossoms having a very strong fragrance, (c) forms dense dark green foliage having a semi-glossy aspect that contrasts well with the blossom coloration, and (d) is particularly well suited for growing as attractive ornamentation in the landscape;

substantially as herein shown and described.

* * * * *

MEIFAISSEL